(12) United States Patent
Harel

(10) Patent No.: US 7,998,502 B2
(45) Date of Patent: Aug. 16, 2011

(54) ENCAPSULATED VACCINES FOR THE ORAL VACCINATION AND BOOSTERING OF FISH AND OTHER ANIMALS

(75) Inventor: Moti Harel, Pikesville, MD (US)

(73) Assignee: Advanced Bionutrition Corp., Columbia, MD (US)

(*) Notice: Subject to any disclaimer, the term of this patent is extended or adjusted under 35 U.S.C. 154(b) by 0 days.

(21) Appl. No.: 12/409,607

(22) Filed: Mar. 24, 2009

(65) Prior Publication Data

US 2009/0238845 A1 Sep. 24, 2009

Related U.S. Application Data

(60) Provisional application No. 61/038,809, filed on Mar. 24, 2008.

(51) Int. Cl.
*A61K 39/00* (2006.01)
*A61K 39/38* (2006.01)
*A61K 45/00* (2006.01)
*A61K 47/00* (2006.01)
*A61K 38/00* (2006.01)
*A61K 35/00* (2006.01)
*A23K 1/165* (2006.01)

(52) U.S. Cl. .......... 424/442; 424/184.1; 424/278.1; 424/439; 424/451; 424/489; 424/490; 424/780; 514/1.2

(58) Field of Classification Search .......... None
See application file for complete search history.

(56) References Cited

U.S. PATENT DOCUMENTS

| | | | |
|---|---|---|---|
| 6,485,950 B1 * | 11/2002 | Kumar et al. | 435/189 |
| 7,670,627 B2 * | 3/2010 | Shefer et al. | 424/502 |
| 2004/0081638 A1 | 4/2004 | Kyle | |
| 2004/0177392 A1 | 9/2004 | Barratt et al. | |
| 2004/0224019 A1 * | 11/2004 | Shefer et al. | 424/469 |
| 2006/0024404 A1 | 2/2006 | Kyle | |
| 2006/0120999 A1 | 6/2006 | Dhar | |
| 2006/0121468 A1 | 6/2006 | Allnutt et al. | |
| 2006/0127453 A1 | 6/2006 | Harel | |
| 2006/0130162 A1 | 6/2006 | Kyle et al. | |
| 2007/0082008 A1 | 4/2007 | Harel et al. | |
| 2007/0292952 A1 | 12/2007 | Dhar et al. | |
| 2008/0044481 A1 | 2/2008 | Harel | |
| 2008/0194504 A1 | 8/2008 | Kyle | |
| 2008/0268063 A1 * | 10/2008 | Jon et al. | 424/491 |
| 2009/0181363 A1 | 7/2009 | Dhar | |
| 2009/0238845 A1 * | 9/2009 | Harel | 424/234.1 |
| 2009/0238890 A1 | 9/2009 | Piechocki et al. | |
| 2009/0246184 A1 | 10/2009 | Harel et al. | |
| 2010/0143481 A1 * | 6/2010 | Shenoy et al. | 424/489 |

FOREIGN PATENT DOCUMENTS

| | | |
|---|---|---|
| CA | 2659917 A1 * | 9/2009 |
| EP | 1534307 A1 * | 6/2005 |
| EP | 2105129 A2 * | 9/2009 |
| WO | WO9531184 | 11/1995 |
| WO | WO 02/076391 | 10/2002 |
| WO | WO 03/089579 | 10/2003 |
| WO | WO03086454 | 10/2003 |
| WO | WO 03/103692 | 12/2003 |
| WO | WO 2004/043139 | 5/2004 |
| WO | WO2004043140 | 5/2004 |
| WO | WO 2005/017134 * | 2/2005 |
| WO | WO 2005/115341 A2 * | 12/2005 |
| WO | WO 2006/122299 | 11/2006 |
| WO | WO2007058462 | 5/2007 |
| WO | WO 2007/067207 | 6/2007 |
| WO | WO 2007/104562 * | 9/2007 |
| WO | WO 2007/117511 | 10/2007 |
| WO | WO 2008/063910 A2 * | 5/2008 |
| WO | WO 2008/076975 | 6/2008 |
| WO | WO 2008/140610 | 11/2008 |
| WO | WO 2008/154294 A1 * | 12/2008 |
| WO | WO 2010/042555 A2 * | 4/2010 |

OTHER PUBLICATIONS

Friend, Advanced Drug Delivery Reviews. 2005, 57:247-265.*
Benyacoub, B., Rochat, F., K.Y, S., Rochat, I., Antille, N., Cherbut, C., von der Weid, T., Schiffrin., E.J., Blum, S., 2008. Feeding a Diet Containing a Fructooligosaccharide Mix Can Enhance *Salmonella* Vaccine Efficacy in Mice. J. Nutr. 138, 123-129.
Dang, J.M., Leong, K.W., 2006. Natural polymers for gene delivery and tissue engineering. Adv. Drug Deliv. Rev. 58(4), 487-499.
van der Lubben, I.M., Verhoef, J.C., Borchard, G., Junginger, H.E., 2001. Chitosan for mucosal vaccination. Advanced Drug Delivery Reviews 52 (2), 139-144.
van der Lubben, I.M., Verhoef, J.C., van Aelst, A.C., Borchard, G., Junginger, H.E., 2001. Chitosan microparticles for oral vaccination: preparation, characterization and preliminary in vivo uptake studies in murine Peyer's patches. Biomaterials 22(7), 687-694.
Wu, X.S., 2004. Synthesis, characterization, biodegradation, and drug delivery application of biodegradable lactic/glycolic acid polymers: Part III. Drug delivery application Artif. Cells Blood Substit. Immobil. Biotechnol 32(4), 575-591.
S. Bravo and PJ Midtlyng (2007) The Use of Fish Vaccines in the Chilean Salmon Industry 1999-2003. Aquaculture 270: 36-42.

(Continued)

*Primary Examiner* — Nita M Minnifield
(74) *Attorney, Agent, or Firm* — Marianne Fuierer; Moore & Van Allen, PLLC

(57) ABSTRACT

The invention relates to a composition comprising a pharmaceutically active agent and a bioadhesive delivery system that provides for the oral delivery of a vaccine to animals, particularly aquatic animals.

11 Claims, No Drawings

OTHER PUBLICATIONS

Chopra, S., Mandi, S., Kau, r.J., Iqbal, Z., Talegaonkar, S., F.J, A., 2006. Advances and potential applications of chitosan derivatives as mucoadhesive biomaterials in modern drug delivery. J. Pharm. Pharmacol. 58(8), 1021-1032.

Malik, D.K., Baboota, S., Ahuja, A., Hasan, S., Ali, J., 2007. Recent advances in protein and peptide drug delivery systems. . Curr. Drug Deliv. 4(2), 141-151.

Kim, T.J., Kim, K.H., Lee, J.I., 2007. Stimulation of mucosal and systemic antibody responses against recombinant transferrin-binding protein B of *Actinobacillus pleuropneumoniae* with chitosan after tracheal administration in piglets. J. Vet. Med. Sci. 69(5), 535-539.

Kang, M.L., Jiang, H.L., Kang, S.G., Guo, D.D., Lee, D.Y., Cho, C.S., Yoo, H.S., 2007. Pluronic F127 enhances the effect as an adjuvant of chitosan microspheres in the intranasal delivery of *Bordetella bronchiseptica* antigens containing dermonecrotoxin. Vaccine 25(23), 4602-4610.

Davis, S.S., 2006. The use of soluble polymers and polymer microparticles to provide improved vaccine responses after parenteral and mucosal delivery. Vaccine 24(2), 7-10.

Siwicki, A.K. et al. "Dietary intake of immunostimulants by rainbow trout affects non-specific immunity and protection against furunculosis." Veterinary Immunology and Immunopathology, vol. 41, No. 1-2, May 1, 1994, pp. 125-139.

\* cited by examiner

ENCAPSULATED VACCINES FOR THE ORAL VACCINATION AND BOOSTERING OF FISH AND OTHER ANIMALS

CROSS-REFERENCE TO RELATED APPLICATIONS

This application claims priority to U.S. Provisional Application No. 61/038,809 filed in the United States Patent and Trademark Office on Mar. 24, 2008, the contents of which are hereby incorporated by reference herein for all purposes.

BACKGROUND OF THE INVENTION

1. Field of the Invention

The present invention relates to a composition comprising a pharmaceutically active agent, such as, but not limited to, an immunogenic agent (e.g., a vaccine), and a bioadhesive delivery system, that allows the oral administration and delivery of the pharmaceutically active agent essentially unaltered to the intestinal mucosa.

2. Background of Related Art

Orally delivered pharmaceutically active agents present a significant problem in transiting an animal's stomach, an organ whose contents represent a harsh digestive environment consisting of low pH and enzymes specifically designed to denature proteins. As a consequence, orally delivered bacterin or subunit vaccines have not been proven to be efficacious since the antigens are generally modified by the stomach prior to presentation to the immuno-responsive cells of the gut mucosa. A number of approaches have been tested to provide an oral delivery vehicle that would transit the stomach but most have been unsuccessful at the commercial scale. One approach involves the transient changing of the stomach pH, neutralizing gastric enzymes and stimulating the mucosal immune response.

In 2003 about 200 million fish were vaccinated in Chile, primarily for Yersiniosis, Salmonid Ricketsial Septicaemia, and Invectious Pancreatic Necrosis (Bravo, 2007). Of the more than 20 vaccines for aquacultured fish were brought to the Chilean market from 1999-2003, none were orally delivered vaccines.

Salmon Rickettsial Septicaemia (SRS) is a pathology of salmonid fish caused by the intracellular bacterium *Piscrickettsia salmonis* and is a major infectious disease in the Chilean salmon industry with annual losses exceeding 20%. Unlike other bacterial diseases, the anti-SRS vaccination is not as effective in preventing the disease or in reducing the need for post-infection medication. This is because of a gradual diminishing of the SRS immunogenicity in the vaccinated fish. Boostering the vaccine at a later stage should allow the continued protection of the animals throughout the entire commercial growing period. However, it is extremely difficult and economically impractical to provide parenteral vaccine boosters to large animals in the grow-out net pens.

Almost all existing vaccines are delivered to aquatic animals by injection, which is traumatic, inconvenient, time consuming, expensive, has a number of side effects, and may fail to induce an appropriate immunogenic response in mucosal tissues. Thus, a method and system for delivery that avoids these disadvantages would be advantageous.

Perhaps the most well known antigen delivery systems are those derived from the linear polymeric esters of lactic acid and glycolic acid (i.e., poly DL-lactide-co-glycolide, PLGA, reviewed by Wu (Wu, 2004). In such systems, immunogenic subunit vaccine components have been captured in poly-acrylate and poly-glycolide/lactide beads or liposome-like vesicles through processes utilizing volatile organic solvents such as dichloromethane or chloroform. The solvents are used to form emulsions of polymer solutions or dried lipid films. Encapsulation of antigens into PLGA microcapsules affords a number of advantages including rapid degradation by hydrolysis and subsequent penetration of the Peyer's Patches (concentrated sites of lymphocytic tissue in the intestinal mucosa of higher vertebrates but not in fish). A major disadvantage of PLGA microcapsules is the requisite use of organic solvents. Contact with organic solvents can inactivate or reduce the efficacy of the vaccine by altering the immunogenicity of surface proteins critical to induction of humoral or cellular immune responses. Additionally, Poly-acrylate and poly-glycolide/lactide processes typically result in microbeads with extremely low immunogen or antigen capture efficiency.

Polymer microspheres and lamellar particles (e.g., liposomes) have been employed for the improved parenteral and mucosal administration of antigens. Because vaccines themselves may not be efficiently recognized and taken up by mucosal lymphocytes, they typically need to be co-administered with penetration enhancers or adjuvants. Different classes of polymer mixtures are known for potential use as Mucoadhesives (Malik et al., 2007). These include synthetic polymers such as poly (acrylic acid) (PAA), hydroxypropyl methylcellulose and poly(methylacrylate) derivatives, as well as naturally occurring polymers such as hyaluronic acid and chitosan.

Chitosan has been used for a variety of applications as a biomaterial for tissue engineering, wound healing, and as an excipient for drug delivery (Chopra et al., 2006; Dang and Leong, 2006). Chitosan has occasionally been tested as an adjuvant for mucosal application (Kim et al., 2007), but it is typically applied directly to a mucosal surface such as intra-nasal application in order to obtain IgA response in the nasopharyngeal mucosa of terrestrial animals (Kang et al., 2007). However, the use of chitosan in vaccine delivery remains very limited due to poor physicochemical characteristics such as a high transition temperature and interfacial free energy, resulting in a suboptimal interaction with mucosal surfaces and loose interpenetration and interdiffusion of the polymer. This problem is further compounded when used for poikilotheric lower vertebrates like salmonid fish. Chitosan also has the additional disadvantage of a low mechanical strength and solubility.

Thus, there remains a need for effective systems and processes for microencapsulation of immunogenic substances with polymers having superior adhesive and cohesive properties.

SUMMARY OF THE INVENTION

The present invention overcomes the shortcomings of the above-discussed encapsulation systems, wherein the present invention discloses a composition designed for an oral delivery of a primary and or booster vaccination that can be used for animals housed in the not only in hatchery but also grow-out pens. The exceptional mucoadhesive properties of compositions of the present invention provide a successful method of transmucosal drug delivery, especially for lower vertebrates with less developed digestive system and no Peyer's Patches such as fish.

One aspect of the present invention provides for a bioadhesive delivery system comprising a composition including a cationic polysaccharide, a neutral polysaccharide in combination with a pharmaceutically active agent, such as an immunogenic agent. Surprisingly, the immunogenic agent when administered with the cationic polysaccharide and neutral polysaccharide results in a similar or better immunologic induction than parenteral administration of the pharmaceutically active agent.

Another aspect of the present invention provides for a composition comprising a cationic polysaccharide, a neutral polysaccharide in combination with a pharmaceutically active agent, wherein the cationic polysaccharide is chitosan and the neutral polysaccharide is a fructan, and more preferably, an inulin or fragments thereof.

A further aspect of the present invention provides for oral delivery of a pharmaceutically active agent, such as an antigen, wherein the pharmaceutically active agent is released at the site of action (i.e., the Gut Associated Lymphoid Tissue; GALT) along the foregut and hindgut of the animal. Importantly, the delivery vehicle comprising a cationic polysaccharide, a neutral polysaccharide in combination with the pharmaceutically active agent, further provides protection of the antigen during transit through the stomach of the animal and then provides a gradual dissolution, corresponding to the hindgut transit time of about 2 hours, and permits reproducible release of the antigen therein.

A still further aspect of the present invention provides for a method of producing a bioadhesive delivery vehicle for vaccination of animals, such as aquatic animals, wherein the delivery vehicle is in a form of dry microparticles comprising an immunogenic agent embedded or impregnated in a composite matrix of cross-linked chitosan, oligosaccharides, saccharides. Any applicable oligosaccharides may be used in the composition. Common oligosaccharides include fructo-oligosaccharides (FOS), galacto-oligosaccharides (GOS), and inulins. In a preferred embodiment of the invention, the method comprises producing a bioadhesive delivery vehicle containing an SRS vaccine for use in salmonid fish.

Another aspect of the present invention provides for a feed regime wherein animals are fed a bioadhesive delivery vehicle comprising a cationic polysaccharide, a neutral polysaccharide in combination with a pharmaceutically active agent, for the oral vaccination of animals. In a preferred embodiment, the vaccinated animal is a fish and, in a more preferred embodiment the fish are salmonids and the oral vaccination, or booster, is to prevent the disease known as SRS.

A still further aspect of the present invention provides for a composition for stablilizing and delivery of a pharmaceutically active agent to the gut, the composition comprising chitosan and inulin in combination with an emulsifier/sugar complex, wherein the emulsifier/sugar complex comprises lecithin and is in an amount sufficient to mediate the interaction between inulin and the hydrophobic amine residues of chitosan.

Another aspect of the present invention provides for a method of preparing a composition for oral delivery of a pharmaceutically active ingredient comprising:
a) preparing an acidic aqueous solution comprising at least one bioadhesive polymer, wherein the bioadhesive polymer is chitosan and the acidic solution has a pH low enough to gelatinize the chitosan;
b) combining an oligosaccharide, such as inulin, into the solution with the gelatinized chitosan to form a inulin-chitosan solution;
c) combining an emulsifier with a sugar, wherein the sugar and emulsifer form a sugar/emulsifier complex;
d) introducing the sugar/emulsifier complex into the inulin-chitosan solution to form a smooth emulsion while maintaining the acidic pH of the solution;
e) adding a pharmaceutically active agent into the smooth emulsion; and
f) precipitating the emulsion into a phosphate containing cross-linking solution.

Other aspects and advantages of the invention will be more fully apparent from the ensuing disclosure and appended claims.

DETAILED DESCRIPTION OF THE INVENTION

Definitions

In describing the present invention, the following terminology is used in accordance with the definitions set out below.

A "pharmaceutically active agent" is defined as any biological material that results in the prevention, cure, or mitigation of a disease in any animal. All vaccines are intended to be included in this definition of pharmaceutically active agents.

"Microencapsulation" is defined as a process that produces a composition containing a pharmaceutically active agent that is in the form of a microparticle in the size range of 10 to 1000 um, or a composition that can be milled to a microparticle in the size range of 10 to 1000 um.

An "immunogen" or an "immunogenic agent" is defined as a substance or a composition of matter, which is capable of mounting a specific immune response in an animal. Immunogenic agents would include immunogenic peptides and proteins including mixtures comprising immunogenic peptides and/or proteins (e.g., bacterins); intact inactive, attenuated, and infectious viral particles; intact killed, attenuated, and infectious prokaryotes; intact killed, attenuated, and infectious protozoans including any life cycle stage thereof, and intact killed, attenuated, and infectious multicellular pathogens, recombinant subunit vaccines, and recombinant vectors to deliver and express genes encoding immunogenic proteins (e.g., DNA vaccines).

"Vaccination" is defined as a process that results in a specific immune response generated by an animal against an immunogen or an immunogenic agent.

A "bioadhesive delivery system" is defined as a composition that results in the delivery of an immunogen or an immunogenic agent to the desired location in the gut associated lymphoid tissue (GALT) of the intestinal mucosa.

A "mucoadhesive" molecule is a component of a bioadhesive delivery system that specifically binds to mucosal tissues. Such molecules include, but are not limited to chitosan, hyloronic acid, gum Karaya, and cationic guar.

The present invention provides an improved immunogenic substance for oral delivery. The invention is based on the discovery of unexpected synergetic properties of a complex mixture of chitosan and a fructan.

Fructans or fructosans are oligosaccharides or polysaccharides comprising a sequence of anhydrofructose units optionally combined with one [lacuna] more different saccharide residues of the fructose. Fructans can be linear or branched. Fructans can be products obtained directly from a plant or microbial source or else products with a chain length which has been modified (increased or reduced) by splitting, synthesis or hydrolysis, in particular of the enzymatic variety. Fructans generally have a degree of polymerization from 2 to approximately 1 000 and preferably from 3 to approximately 60.

The fructan is preferably used in an amount of between 0.01 and 20% by weight with respect to the total weight of the composition. More preferably, this amount is between 0.05 and 15% by weight with respect to the total weight of the composition and more preferably between 1 and 10% by weight.

The preferred fructans are inulins. Inulins refer to a group of naturally-occurring fructose-containing oligosaccharides. Because inulin fiber is resistant to digestion in the upper gastrointestinal tract (i.e., the stomach), it reaches the large intestine essentially intact, where it can be digested by indigenous bacteria. Inulins generally consist of chains of polyfructose in which the fructose units are connected to each other mostly or exclusively by β-(2-1) linkages. Inulin occurs in nature, in general, as a polydisperse mixture of polyfructose chains, most of which terminate in one glucosyl unit. They are derived from the roots of chicory (*Cichorium intybus*), the dahlia and Jerusalem artichokes. Additonally, inulin can be obtained from bacterial syntheses or can be made in vitro by enzymatic synthesis starting from sucrose. It has been shown that inulin stimulates mucosal immunity and seems to improve efficacy of a *Salmonella* vaccine in mice (Benyacoub et al., 2008). Although the mechanism of action is unclear, several studies have proposed that inulin may induce changes in colonic epithelium by stimulating proliferation in the crypts, increasing the concentration of polyamines, changing the profile of mucins, and/or modulating endocrine as well as immune functions (Roberfroid, 2005). The average degree of polymerisation of inulins marketed as nutritional supplements is 10 to 12. Inulins stimulate the growth of Bifidobacterium species in the large intestine.

Fructooligosaccharides or FOS typically refer to short-chain oligosaccharides comprised of D-fructose and D-glucose, containing from three to five monosaccharide units. FOS, also called neosugar and short-chain FOS, are produced on a commercial scale from sucrose using a fungal fructosyl-transferase enzyme. FOS are resistant to digestion in the upper gastrointestinal tract. They act to stimulate the growth of Bifidobacterium species in the large intestine.

Chitosan is a linear cationic polysaccharide which is gelled or crosslinked in the presence of anions, such as citrate, phosphate or sulfate. Chitosan has also been shown to possess useful properties such as non-toxicity, high biocompatibility and non-antigenicity. While chitosan is itself largely insoluble in water, solubility markedly increases if the pH is shifted towards the acid condition. To obtain an appreciable polymer concentration, it is therefore necessary to prepare the solution or dispersion with simultaneous use of an acid. To be able to more easily remove this acid from the composition later, it turned out that the acid should have a low boiling point, namely preferably maximally 140° C., in particular maximally 120° C., especially preferred maximally 100° C., and most preferably maximally 80° C., such as hydrogen chloride, hydrogen bromide, trifluoracetic acid, formic acid and acetic acid. Other suitable are also acids forming a lower-boiling binary azeotrope with water, such as acetic acid or propionic acid.

Chitosan can be obtained through the deacetylation of chitin, the major compound of exoskeletons in crustaceans. Chitosan [a-(1~4)-2-amino-2-deoxy-β-D-glucan], a muco-polysaccharide closely related to cellulose, exhibits chemical properties that are determined by the molecular weight, degree of deacetylation, and viscosity. Chitosan can form microparticles and nanoparticles that can encapsulate large amounts of antigens (van der Lubben et al., 2001; Davis, 2006). In the acidic environment of the stomach, chitosan retains its positive charges that hold the particle together. It has been shown that ovalbumin loaded chitosan microparticles can be taken up by the Peyer's Patches of the gut associated lymphoid tissue of higher vertebrates. Additionally, after co-administering chitosan with antigens in nasal vaccination studies in a strong enhancement of both mucosal and systemic immune responses in mice was observed (van der Lubben et al., 2001).

Preparation of the Bioadhesive Delivery System specific to gut mucosa: An aqueous solution or suspension of a pharmaceutically active agent (e.g., an immunogenic agent, including, but not limited to vaccines) and, if desired, an adjuvant including, but not limited to beta glucan, lipopolysaccharide, aluminium salts, squalene and/or virosomes, is dissolved or suspended in an aqueous solution of a suitable mucoadhesive polymer such as, but not limited to, chitosan and a suitable oligosaccharide such as, but not limited to, inulin. The resulting solution/suspension is then dispersed directly or by atomization into an aqueous cross-linking solution containing water-soluble phosphate salts. Upon contact, a salt exchange reaction (cross-linking) takes place, resulting in the formation of beads or capsules in which the pharmaceutically active agent is retained. The resulting suspension of microparticles containing the encased pharmaceutically active agent is then collected, dried, and milled if necessary to form particles having a size range from 10-1000 micron. Details of the preparation are set out in the series of steps described below:

Step (a): Preparation of complex mucoadhesive hydrogel. A mucoadhesive polymer such as chitosan, at a concentration of 1 to 10% (w/w), is dispersed in 1-5 N acetic acid solution at a temperature range of 20 to 65° C. until all polymer granules are fully dissolved. Preferably, the chitosan is at least 85% deacetylated. Additionally it is preferred that the pH is of the acidic aqueous solution is from about 2 to about 4. The gelatinization of the polymer granules is required in order to prepare a microparticle possessing the immunogenic property.

In embodiments of the invention, indigestible short chain oligosaccharide components are also be added at a concentration of from about 1 to 30% (w/w) to improve protection of the antigen from stomach acidity, bile acids and proteases and increase the intestinal adsorption of the antigen. Examples of applicable materials include, but not limited to, chitosan oligosaccharide (COS), inulin, fructooligosaccharides (FOS), and dextrin. These absorption-increasing components may dissolve more readily in intestinal juices than other matrix materials. Consequently, permeability and biodegradability of the matrix polymer can be increased, resulting in an improved release of the pharmaceutically active agent at the desired location in the GALT of the intestinal mucosa.

Step (b): Complex formation of the mucoadhesive material and a short chain oligosaccharide. Without wishing to be bound by theory, it is believed that the processes described herein yield a novel complex composition mediated by an emulsifier/sugar complex and comprising polysaccharides and oligosaccharides in the form of a complex matrix having an insoluble microparticle nature. The emulsifier and sugar molecules mediate the interaction between hydroxyl residues of the short chain oligosaccharide and hydrophobic amine residues of the cationic polysaccharide. Generally, the emulsifiers can be, but are not limited to, any of monoglycerides, sorbitan esters, propylene glycol esters, lecithin, polysorbates and sucrose esters of medium and long chain saturated fatty acids, and the sugars will be any mono- or disaccharides such as, but not limited to glucose, fructose, or sucrose. A solution comprising an emulsifier/sugar mediating mixture (containing 0.5 to 12.5% w/w emulsifier and 5-30% w/w sugar) is added to the gelatinized mucoadhesive polysaccharide and short chain oligosaccharide solution at a temperature range of from 20 to 65° C. and pH 3-5 until a smooth and stable emulsion has formed. This emulsion is stabilized by the interaction between positive charge of the cationic polysaccharide, the emulsifier and hydroxyl groups of the short chain oilgosaccharides. The increased hydrophobicity and elasticity of the mucoadhesive polysaccharide and emulsifier helps delay or prevent penetration of water or gastric juices into the matrix once formed into microparticles. The acidity of the product slurry is then gradually increased to pH 6.2 by the addition of base such as, but not limited to sodium hydroxide.

Step (c): Addition of immunogenic substance and cross-linking reaction. A solution comprising a pharmaceutically active agent. such as, but not limited to, an immunogen or immunogenic antigen is dissolved into the slurry described in Step (b) above, and the composition can be dried to produce a powder by a number of art-recognized methods including, but not limited to, low temperature spray drying, belt drying, freeze drying, drum drying or flash drying. In a preferred embodiment, the dispersion is passed through a tube or needle ranging from 10 um to 1,000 um in diameter to fall dropwise or in a continuous stream into a cross-linked solution containing 1-10% sodium triphosphate in water. Alternatively, the slurry can be spray-atomized into an aqueous solution containing 1-10% sodium triphosphate. Wet particles can be harvested from the cross-linking bath by any suitable means well known in the art (e.g., filtration, centrifugation, etc) and mixed with any acceptable thickening agent such as methylcellulose, pectin, alginate, xanthan gum, carboxymethyl cellulose, hydroxypropyl cellulose, and the like, and sprayed onto feed pellets (i.e., top-coated). Alternatively, the wet particles can be dried using conventional processes well known in the art such as, but not limited to, vacuum drying, spray drying, and tunnel drying, milled to the appropriate size class if necessary, and then mixed with fish oil or other edible oils prior to application to a standard commercially available feed by top-coating using methods known in the art.

Feeding strategy for oral vaccination: Juvenile fish having a mature immune system (for Atlantic Salmon generally at about 0.5 g) are ready to be orally vaccinated. However the instant invention provides a flexible strategy that also allows the vaccination of, or boosting the immunogenic response of larger fish and other animals. To effectively induce the immunogenic response, the fish or other animals should be orally fed in a single event at a similar or greater dose of immunogen that is usually provided by injection. To maximize the fish immunogencity and depending the on Immunogen type, fish size and responsiveness, this single feeding event may be repeated (e.g., every three days for up to ten feeding events).

EXAMPLES

Example 1

Production of Bioadhesive Microparticles

Chitosan (Sigma, St. Louis, Mo.), (1gram) was dissolved 50 ml of 0.5N acetic acid at 50° C. Instant Inulin (Cargil, Minneapolis, Minn.), sucrose, and soy lecithin (Archer-Daniels-Midland Co., Decatur, Ill.) were added to the acidic slurry and allowed to complex with the chitosan for 30 min. The amount of each compound added to the acidic solution is shown in Table 1, as set forth below. The pH of the acidic complex slurry was then adjusted to 6.2 with sodium hydroxide and the slurry allowed to cool down to room temperature. The slurry was then spray atomized into a 5% w/w sodium triphosphate and 1% w/w sodium chloride bath to form microparticles in a size range between 10 um and 100 um. The microparticles were washed with tap water on a fine mesh screen, dipped into a 30% sucrose solution and kept refrigerated at 4° C. until use. The composition of the microparticles is provided in Table 1.

TABLE 1

| Microparticle composition (g dry weight/100 g solution) | |
|---|---|
| Chitosan | 1 g |
| Soy lecithin | 3 g |
| Inulin | 30 g |
| Sucrose | 16 g |
| Water | 50 g |

Example 2

Production of Bioadhesive Particles containing Salmonid Rickettsial Septicaemia (SRS) Vaccine A complex slurry at pH 6.2 was prepared as described in Example 1. A solution containing attenuated SRS vaccine ($5 \times 10^{11}$/ml SRS bacteria) without adjuvant (commercially available from Centrovet, Santiago, Chile) was mixed into the slurry (3% v/v). The slurry was then spray atomized into 5% w/v sodium triphosphate and 1% w/v sodium chloride bath to form microparticles in a size range between 10 um and 100 um. The microparticles were allowed to harden for 1 hour and then washed with sterile water on a fine mesh screen, and dipped into a 30% (w/v) sucrose solution. Wet particles were then freeze-dried over night and the dry powder refrigerated at 4° C. until use. The composition of the microparticles is provided in Table 2.

TABLE 2

| Microparticle composition (g dry weight/100 g solution) | |
|---|---|
| Chitosan | 1 g |
| Soy lecithin | 3 g |
| Inulin | 30 g |
| SRS vaccine | 3 ml |
| Sucrose | 16 g |
| Water | 47 g |

Example 3

Production of Atlantic Salmon Feed Containing SRS Immunogenic Microparticles

Fifteen grams of dry SRS immunogenic microparticles prepared as in Example 2 were mixed with 30 g of fish oil. The oily mixture was sprayed on 1 kg of standard commercial feed for Atlantic salmon juveniles (Ewos, Km 20 Coronel, Concepción, Chile) and the oral vaccination feed was stored in 4° C. during its use.

Example 4

Oral Vaccination of Atlantic Salmon Against Using the Immunogenic Microparticles of the Present Invention Atlantic salmon juveniles ca. 10 g size are stocked at 30 kg per m3 of fresh water and at temperature of 12° C. Water quality is maintained by rapidly exchanging the tank water through mechanical and biofiltration systems. Fish are fed 4 times daily a total ration of 2% body weight on a commercial feed. Every 3 days the diet is replaced with a 2% vaccine topcoated diet as described in Example 3 for a period up to 30 days. Animals will develop antibodies to the orally-deliver vaccine over the subsequent two months.

Example 5

Production of Bioadhesive Particles Containing Swine Influenza Vaccine

A complex slurry at pH 6.2 was prepared as described in Example 1. A solution containing FLUSURE™ (Pfizer Animal Health), a vaccine against Swine Influenza Virus Type A, subtypes H1N1 and H3N2 was mixed into the slurry (3% v/v). The slurry was then introduced into a bath containing 5% w/v sodium triphosphate and 1% w/v sodium chloride through a 500 micron needle to form long noodles. The noodles were allowed to cross-link for 1 hour and then washed with sterile water on a fine mesh screen, dipped into a 30% (w/v) sucrose solution, freeze dried, and then milled to a particle size of 200 microns. The composition of the particles is provided in Table 3.

TABLE 3

| Noodle composition (g dry weight/100 g solution) | |
|---|---|
| Chitosan | 1 g |
| Soy lecithin | 3 g |
| Inulin | 30 g |
| FluSureTM vaccine | 3 ml |
| Sucrose | 16 g |
| Water | 47 g |

Example 6

Oral Vaccination of Swine Against Swine Flu Using the Immunogenic Microparticles of the Present Invention Fifteen grams of dry FLUSURE™ immunogenic microparticles prepared as in Example 5 were mixed with 30 g of soybean oil. The oily mixture was sprayed on 1 kg of standard commercial feed for swine (Cargill Corp) and the oral vaccination feed was stored in 4° C. prior to its use.

Young pigs are fed with the oral vaccination feed every 3 days for a period of 21 days after maternally derived antibodies have declined. Animals will develop antibodies to the orally-deliver vaccine over the subsequent two months.

Example 7

Production of Bioadhesive Particles Containing Salmonella Vaccine for Poultry A complex slurry at pH 6.2 was prepared as described in Example 1. A solution containing NOVILIS SALENVAC™ (Intervet Corp), an inactivated Salmonella vaccine for the elimination of S. enteritidis in both poultry meat and eggs was mixed into the slurry (3% v/v). The slurry was then introduced dropwise into a bath containing 5% w/v sodium triphosphate and 1% w/v sodium chloride through a 500 micron needle to form droplets of about 2-3 mm in diameter. The microspheres were allowed to cross-link for 1 hour and are then washed with sterile water on a fine mesh screen, dipped into a 30% (w/v) sucrose solution, freeze dried, and then milled to a particle size of 200 microns. The composition of the particles is provided in Table 4.

TABLE 4

| Noodle composition (g dry weight/100 g solution) | |
|---|---|
| a) Chitosan | 1 g |
| b) Soy lecithin | 3 g |
| c) Inulin | 30 g |
| d) Nobilis Salenvac ™ vaccine | 3 ml |
| e) Sucrose | 16 g |
| f) Water | 47 g |

Example 8

Oral Vaccination of Poultry Against Salmonella Using the Immunogenic Microparticles of the Present Invention Fifteen grams of dry NOBILIS SALENVAC™ immunogenic microparticles prepared as in Example 7 were mixed with 30 g of soybean oil. The oily mixture was sprayed on 1 kg of standard commercial feed for laying hens (Cargill Corp) and the oral vaccination feed was stored in 4° C. prior to its use.

Chickens at 10-12 weeks of age are fed with a single dose of the oral vaccination feed and a booster dose is provided between 14-18 weeks of age at an interval of every 3 days for a period of 21 days.

REFERENCES

The contents of all references cited herein are incorporated by reference herein for all purposes.

Benyacoub, B., Rochat, F., K. Y, S., Rochat, I., Antille, N., Cherbut, C., von der Weid, T., Schiffrin., E. J., Blum, S., 2008. Feeding a Diet Containing a Fructooligosaccharide Mix Can Enhance Salmonella Vaccine Efficacy in Mice. J. Nutr. 138, 123-129.

Chopra, S., Mahdi, S., Kau, r. J., Iqbal, Z., Talegaonkar, S., F. J, A., 2006. Advances and potential applications of chitosan derivatives as mucoadhesive biomaterials in modern drug delivery. J. Pharm. Pharmacol. 58(8), 1021-1032.

Dang, J. M., Leong, K. W., 2006. Natural polymers for gene delivery and tissue engineering. Adv. Drug Deliv. Rev. 58(4), 487-499.

Davis, S. S., 2006. The use of soluble polymers and polymer microparticles to provide improved vaccine responses after parenteral and mucosal delivery. Vaccine 24(2), 7-10.

Kang, M. L., Jiang, H. L., Kang, S. G., Guo, D. D., Lee, D. Y., Cho, C. S., Yoo, H. S., 2007. Pluronic F127 enhances the effect as an adjuvant of chitosan microspheres in the intranasal delivery of Bordetella bronchiseptica antigens containing dermonecrotoxin. Vaccine 25(23), 4602-4610.

Kim, T. J., Kim, K. H., Lee, J. I., 2007. Stimulation of mucosal and systemic antibody responses against recombinant transferrin-binding protein B of Actinobacillus pleuropneumoniae with chitosan after tracheal administration in piglets. J. Vet. Med. Sci. 69(5), 535-539.

Malik, D. K., Baboota, S., Ahuja, A., Hasan, S., Ali, J., 2007. Recent advances in protein and peptide drug delivery systems. Curr. Drug Deliv. 4(2), 141-151.

Roberfroid, M. B., 2005. Introducing inulin-type fructans. Br J Nutr. 93, 13-25.

van der Lubben, I. M., Verhoef, J. C., Borchard, G., Junginger, H. E., 2001. Chitosan for mucosal vaccination. Advanced Drug Delivery Reviews 52 (2), 139-144.

van der Lubben, I. M., Verhoef, J. C., van Aelst, A. C., Borchard, G., Junginger, H. E., 2001. Chitosan microparticles for oral vaccination: preparation, characterization and preliminary in vivo uptake studies in murine Peyer's patches. Biomaterials 22(7), 687-694.

Wu, X. S., 2004. Synthesis, characterization, biodegradation, and drug delivery application of biodegradable lactic/glycolic acid polymers: Part III. Drug delivery application Artif. Cells Blood Substit. Immobil. Biotechnol 32(4), 575-591.

S. Bravo and P J Midtlyng (2007) The Use of Fish Vaccines in the Chilean Salmon Industry 1999-2003. Aquaculture 270: 36-42

That which is claimed is:

1. A composition for oral administration to an animal for intestinal delivery of a pharmaceutically active agent, said composition comprising: a) at least one bioadhesive polymer selected from the group consisting of chitosan, hyaluronic acid, cationic guar, and combinations thereof; wherein the bioadhesive polymer is present at a concentration of between 1% and 10%; b) at least one oligosaccharide selected from the group consisting of inulin, fructooligosaccharide and dextrin, wherein the oligosaccharide is present at a concentration of between 1% and 50%; c) at least one mediating compound having both hydrophilic and lipophilic properties, wherein the mediating compound comprises an emulsifier/sugar complex containing 0.5 to 12.5% w/w emulsifier and 5-30% w/w sugar, and d) a pharmaceutically active agent.

2. The composition of claim 1, wherein the mediating compound comprises at least one emulsifier selected from the group consisting of monoglycerides, sorbitan esters, propylene glycol esters, lecithin, polysorbates and sucrose esters, and/or at least one sugar selected from the group consisting of glucose, sucrose and trehalose.

3. The composition of claim 2, wherein the mediating compound is present at a concentration of between 0.1% and 50%.

4. The composition of claim 1, wherein the pharmaceutically active agent is selected from immunogenic peptides and proteins including recombinant vectors to deliver and express genes encoding immunogenic proteins, intact inactive, attenuated and infectious viral particles; intact killed, attenuated and infectious prokaryotes; intact killed, attenuated and infectious protozoans and intact killed, attenuated and infectious multicellular pathogens.

5. The composition of claim 1, wherein the pharmaceutically active agent is a Salmon Rickettsial Septicaemia (SRS) vaccine.

6. A composition for stabilizing and delivery of a pharmaceutically active agent to the gut of a fish, the composition comprising chitosan and inulin in combination with an emulsifier/sugar complex wherein the emulsifier/sugar complex comprises 0.5 to 12.5% w/w emulsifier and 5-30% w/w sugar, wherein the emulsifier/sugar complex comprises lecithin and is in an amount sufficient to mediate the interaction between inulin and the hydrophobic amine residues of chitosan, and wherein the pharmaceutically active agent is a Salmon Rickettsial Septicaemia (SRS) vaccine.

7. A method for oral vaccination of an animal for intestinal delivery of a pharmaceutically active agent, comprising:
orally administering to the animal a composition according to claim 1.

8. The method of claim 7, wherein the vaccinated animal is a fish, mammal or bird.

9. The method of claim 8, wherein the fish is a salmonid.

10. The method of claim 9, wherein the oral vaccine comprises a Salmon Rickettsial Septicaemia (SRS) vaccine.

11. The composition of claim 1, wherein the composition is sized for oral delivery and having a particle size from about 10 um to 200 um.

* * * * *